United States Patent [19]

Pugia

[11] Patent Number: 5,702,955
[45] Date of Patent: Dec. 30, 1997

[54] ASCORBATE RESISTANT DETECTION OF HYDROGEN PEROXIDE

[75] Inventor: Michael Pugia, Granger, Ind.

[73] Assignee: Bayer Corporation, Elkhart, Ind.

[21] Appl. No.: 446,478

[22] Filed: Oct. 6, 1995

[51] Int. Cl.$^6$ .................................................. G01N 33/00
[52] U.S. Cl. .............................. 436/135; 435/4; 435/28; 435/14; 436/63; 436/66; 436/71; 436/93; 436/94; 436/95; 436/96; 436/97; 436/98; 436/99; 436/127; 436/128; 436/131; 436/164; 436/166; 436/175
[58] Field of Search ............................. 436/63, 66, 71, 436/91, 92, 93, 94, 95, 96, 97, 98, 99, 127, 128, 131, 135, 164, 166, 169, 175; 435/4, 28, 14

[56] References Cited

U.S. PATENT DOCUMENTS

| | | | |
|---|---|---|---|
| 4,455,371 | 6/1984 | Richardson et al. | 435/28 X |
| 4,587,220 | 5/1986 | Mayambala-Mwanika et al. | 436/66 |
| 5,089,420 | 2/1992 | Albarella et al. | 436/66 |
| 5,126,247 | 6/1992 | Palmer et al. | 435/25 |
| 5,173,431 | 12/1992 | Pugia et al. | 436/86 |
| 5,182,213 | 1/1993 | Genshaw et al. | 436/66 |
| 5,264,348 | 11/1993 | Schick et al. | 436/66 X |
| 5,318,894 | 6/1994 | Pugia | 436/66 X |
| 5,374,561 | 12/1994 | Pugia | 436/98 |

FOREIGN PATENT DOCUMENTS

| | | |
|---|---|---|
| 141244 | 5/1985 | European Pat. Off. |
| 59-187266 | 10/1984 | Japan . |
| A1 186668 | 4/1970 | United Kingdom . |

OTHER PUBLICATIONS

N. Ahmad Pak. J. Sci. Ind. Res. 1970, 12, 342–348.
R. Yu. Yuryavichus et al. J. Anal. Chem. USSR 1972, 27, 1006–1008.
I. Jakab et al. Chem. Abstr. 1974, 81, 31561k.
R. H. White–Stevens Clin. Chem. 1982, 28, 578–588.
G. P. Kasidas et al. Clin. Chim. Acta 1987, 164, 215–221.
M. Petrarulo et al. Clin. Chem. 1990, 36, 1642–1645.
X. Li et al. Zhonghua Yixue Jianyan Zazhi 1992, 15, 323–325.
Canty, et al., "Organometallic Compounds Containing a Guanidinium Group. Phenylmercury (II) Derivatives of Creatine and Creatinine," Inorganic Chem. (1978), vol. 17, No. 6, pp. 1467–1471.
Chemical Abstracts, vol. 115, No. 21, 25 Nov. 1991, Columbus, OH, US; abstract no. 227796, Miyauchi et al., "Berlin Acid or Ferrocene Derivatives as Indicator Substrates in Hydrogen Peroxide–Forming Enzymatic Assay for Analyte Determination in Blood" XP0002012573 and JP A 3119997, Kyowa Medix Co., Ltd., Japan (JP). *abstract Chemical Abstracts, vol. 80, No. 13, 1 Apr. 1974, Columbus, OH, USA; abstract no. 071071, DHAR N.R., et al., "Oxidation of Nitrogenous Compounds in Presence of Iron (II) Ions" XP002012572 and Proc. Nat. Acad. Sci., India, Sect. A (PAIAA3); 72; vol. 52 (PT2); pp. 120–124, Univ. Allahabad, Allahabad, India. *abstract.

Clin. Chem. (Winston–Salem N.C.) (CLCHAU, 00099147) 83; vol. 29 (8), pp. 1494–1496, Miles Italiama S.P.A.; Ames Res. Dev. Lab., Cavenago Brianza: 20040, Italy (IT), XP002012571, Fossati P., et al., "Enzymatic Creatinine Assay: A New Colorimetric Method Based on Hydorgen Peroxide Measurement" p. 1496, col. 1.*abstract.

Dietrich, et al., "Anion Coordination Chemistry: Polyguanidinium Salts as Anion Complexones," 16 pages.

Ebermann, et al., "A Nonenzymatic Method for Determination of Hydrogen Peroxide and Organic Peroxides," Analytical Biochemistry (1987), 165, pp. 414–419.

Graf, et al., "Iron–Catalyzed Hydroxyl Radical Formation," J. of Biological Chem. (Mar. 25, 1984), vol. 259, No. 6, pp. 3620–3624.

Hirayama, et al., "Spectrophotometric Catalytic Determination of An Ultratrace Amount of Iron (III) in Water Based on the Oxidation of N,N–Dimethyl–p–phenylenediamine by Hydrogen Peroxide," Anal. Chem. (1988), 60, pp. 2573–2577.

Ozawa, et al., "Formation of Hydroxyl Radical form Reactions of Copper (II) Complexes with Hydrogen Peroxide," Nippon Kagaku Kaishi (1988), vol. 4, pp. 459–465.

Rush, et al., "Reactions of Fe$^{II}$nta and Fe$^{II}$edda with Hydorgen Peroxide," J. Am. Chem. Soc. (1988), 110, pp. 4957–4963.

Rush, et al., "The Reaction between Ferrous Polyaminocarboxylate Complexes and Hydorgen Peroxide: An Investigation of the Reaction Intermediates by Stopped Flow Spectrophotometry," J. of Inorganic Chem. (1987), 29, pp. 199–215.

Primary Examiner—Arlen Soderquist
Attorney, Agent, or Firm—Roger N. Coe

[57] ABSTRACT

The present invention is a method for the detection of hydrogen peroxide in biological fluids or an aqueous solution which involves contacting the solution with an oxidation-reduction indicator and a transition metal complex. The transition metal complex is either a creatinine coordinated with iron or a guanidine coordinated with iron.

25 Claims, 1 Drawing Sheet

ASCORBATE RESISTANT DETECTION OF HYDROGEN PEROXIDE

BACKGROUND OF THE INVENTION

1. Field of the Invention

The invention is a novel methodology to colorimetrically determine the concentration of hydrogen peroxide in biological fluids and in aqueous solutions by contacting a fluid or solution with an indicator and a transition metal complex which is either creatinine coordinated with iron or guanidine coordinated with iron.

2. Description of the Background Art

The detection of hydrogen peroxide in biological fluids such as blood, serum, and urine is useful in the diagnosis of various abnormalities. Hydrogen peroxide is generated as a byproduct of numerous reactions of analytes with enzymes. Tests for the detection of hydrogen peroxide in biological fluids are complicated by the presence of ascorbate, a strong reducing agent which can transfer an electron to the indicator resulting in false negative results. The inclusion of certain metal ion complexes, such as Fe-HEDTA, in the indicator reagent composition essentially eliminates ascorbate interference, however, these metal ion complexes themselves can catalyze the color-forming reaction between the peroxide and the oxidizable dye which can, under some circumstances result in false positives or erroneously high assay results due to additional dye oxidation mediated by the metal ion complex.

There is literature referencing the discovery of creatinine complexes of various transition metals with the exception of iron.

SUMMARY OF THE INVENTION

The objects of the present invention are provided by a method for the detection of hydrogen peroxide in biological fluids. Additionally, the present invention provides a method for the detection of an analyte by reacting the analyte with a compound to produce hydrogen peroxide.

This invention relates to a method for the detection of hydrogen peroxide, comprising (a) adding a transition metal complex and an oxidation-reduction indicator to a solution suspected of containing hydrogen peroxide and (b) analyzing the color transition to detect the presence or concentration of hydrogen peroxide. The transition metal complex may be creatinine coordinated with iron or guanidine coordinated with iron. The creatinine coordinated with iron has the structure:

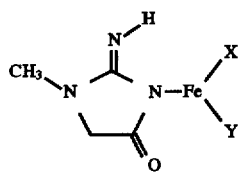

wherein X and Y are independently chosen from the group consisting of creatinine, chloride, fluoride, bromide, iodide, sulfate, phosphate, perchlorate, nitrate, oxalate, sulfide, ammonium, gluconate, cyanide, thiocyanate, catechol, tropolone, phenol, pyridine, buffers such as acetate, citrate, tartaric acid, malonic acid, boric acid, succinic acid, glycerol-2-phosphate, salicylic acid, oxalic acid, and malic acid.

The guanidine coordinated with iron has the structure:

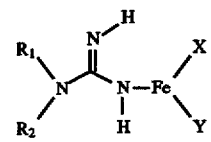

wherein X and Y are independently chosen from the same group as for the iron creatinine complex above and $R_1$ and $R_2$ are independently chosen from the group consisting of alkyl and aryl groups. Examples of $R_1$ and $R_2$ groups are alkyl groups such as $C_nH_{2n+1}$ and $(C_2H_4O)_nH$ wherein n is an integer from 1 to 20, preferably from 1 to 12; and aryl groups such as $C_5H_4Z$, $C_4H_3Z$, and $C_{11}H_6Z$, wherein Z is O, S, N, or CH.

$R_1$ and $R_2$ can optionally be substituted with one or more functional groups which enhance water solubility such as alcohol (—OH), amine (—NH$_2$), carbonyl (—C=O), sulfonic acid (—SO$_3$H), carboxylic acid (—CO$_2$H), fluorine (—F), chlorine (—Cl), bromine (—Br), iodine (—I), phosphonic acid (—P(O)(OH)$_2$), or phosphate (—OP(O)(OH)$_2$). Particularly preferred iron creatinine complexes are those wherein both X and Y are chloride or both X and Y are acetate. Particularly preferred iron guanidine complexes are those wherein both X and Y are sulfate (—SO$_4$) or both X and Y are acetate, and/or wherein $R_1$ is H and $R_2$ is the sulfonic acid-substituted alkyl group —CH$_2$CH$_2$—SO$_3$H; $R_1$ is H and $R_2$ is the amine- and carboxylic acid-substituted alkyl group —(CH$_2$)$_3$CH(NH$_2$)CO$_2$H (arginine); or $R_1$ is H and $R_2$ is the carboxylic acid-substituted aryl group —C$_6$H$_3$(CO$_2$H)$_2$.

The solution containing hydrogen peroxide may be a biological fluid or an aqueous solution. The oxidation-reduction indicator and the transition metal complex may be introduced to the solution by means of a test strip to which they have been applied.

BRIEF DESCRIPTION OF THE DRAWINGS

The advantages of the present invention will become apparent upon reading the following detailed description and upon reference to the accompanying FIGURE, which shows the hydrogen peroxide dose response.

DETAILED DESCRIPTION OF INVENTION

Figure 1:
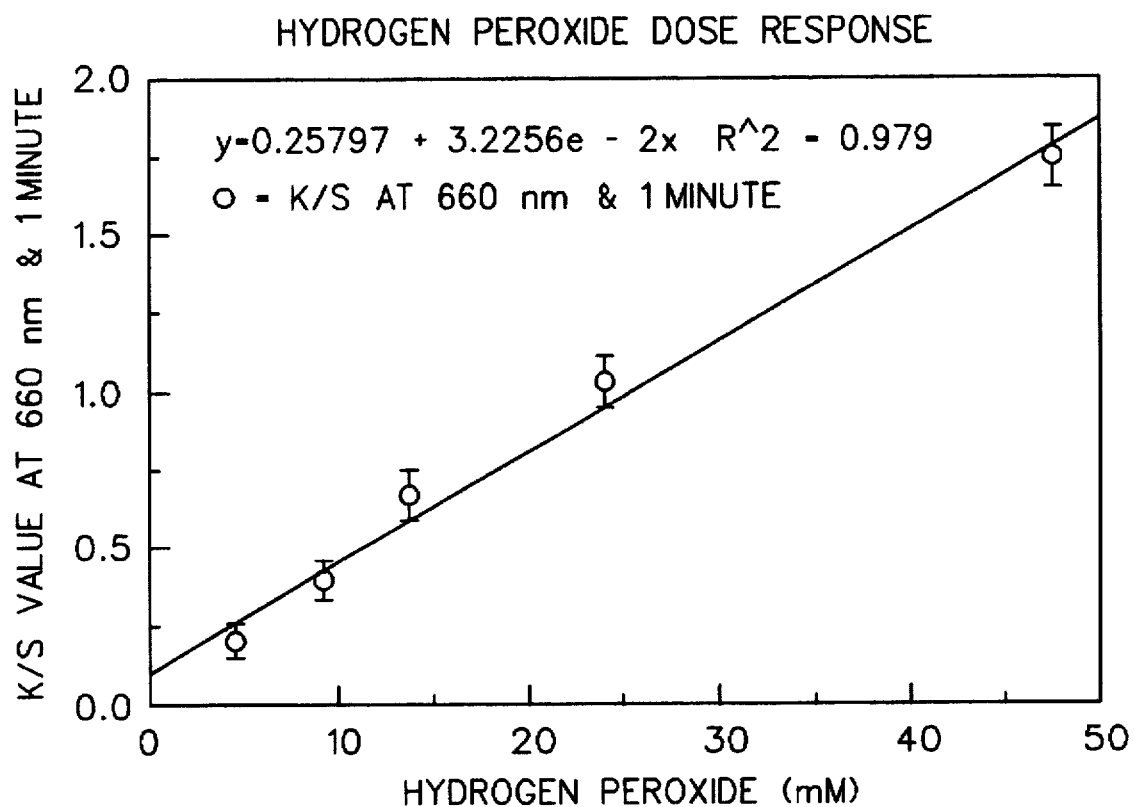

The peroxidase and ascorbate oxidase activities of iron creatinine and iron guanidine complexes were previously unknown. This disclosure describes the first application of iron complexes for the removal of ascorbate interference through the oxidation of ascorbate to dehydroascorbate.

Hydrogen peroxide is produced by numerous reactions carried out in the presence of enzymes. For example:

The determination of the presence or concentration of hydrogen peroxide is a way of determining the presence or concentration of the substrate in a biological fluid.

Table 1 lists examples of substrates and enzymes and the products that they produce. It is not intended to be a complete list of all reactions for which the present invention may be used.

TABLE 1

| Substrate | Enzyme | Product |
| --- | --- | --- |
| Glucose | Glucose oxidase | Gluconic acid |
| Cholesterol | Cholesterol oxidase | Cholest-4-en-3-one |
| D-Aspartate | D-Aspartate oxidase | Oxaloacetate |
| an L-amino acid | L-amino acid oxidase | a 2-oxo acid |
| a D-amino acid | D-amino acid oxidase | a 2-oxo acid |
| $RCH_2NH_2$ | Amine oxidase (flavin-containing) | RCHO |
| Pyridoxamine 5'-phosphate | Pyridoxamine-phosphate oxidase | Pyridoxal 5'-phosphate |
| $RCH_2NH_2$ | Amine oxidase (copper-containing) | RCHO |
| D-Glutamate | D-Glutamate oxidase | 2-oxoglutarate |
| Ethanolamine | Ethanolamine oxidase | glycolaldehyde |
| Putrescine | Putrescine oxidase | 4-aminobutanal |
| Cyclohexylamine | Cyclohexylamine oxidase | Cyclohexanone |
| Peptidyl-L-lysyl-peptide | Protein-lysine 6-oxidase | Peptidyl-allysyl-peptide |
| L-Lysine | L-Lysine oxidase | 2-oxo-6-amino-hexanoate |
| D-Glutamate | D-Glutamate (D-aspartate) oxidase | 2-oxoglutarate |
| L-Aspartate | L-Aspartate oxidase | Oxaloacetate |
| 3-Hydroxyanthranilate | 3-Hydroxyanthranilate oxidase | 6-imino-5-oxocyclo-hexa-1,3-diene-carboxylate |
| D-alanine | D-amino acid oxidase | pyruvate |
| galactose | galactose oxidase | galactonic acid |
| L-tyrosine | polyphenyl oxidase | 4-hydroxyphenyl pyruvate |
| putrescine | plasma amine oxidase | 1-diamine-4-butan-aldehyde |
| L-tryptophan | 1-tryptophan peroxidase | indole |
| uric acid | uricase | allantoin |
| xanthine | xanthine oxidase | uric acid |

The detection of hydrogen peroxide is often carried out by a reaction between hydrogen peroxide, peroxidase, and an oxidation-reduction indicator:

For example, glucose activity may be measured by reacting glucose in the presence of glucose oxidase enzyme to produce hydrogen peroxide. The hydrogen peroxide then reacts with peroxidase to catalyze the oxidation of the indicator to produce a colorimetric response directly proportional to the hydrogen peroxide concentration. However, tests for the detection of hydrogen peroxide in biological fluids are complicated by the presence of ascorbate, a strong reducing agent which can transfer an electron to the indicator resulting in false negative results. The transition metal complexes of the present invention react with hydrogen peroxide to catalyze oxidation of the indicator only in the presence of hydrogen peroxide. Ascorbate causes no interference with the detection of hydrogen peroxide brought about using the transition metal complexes of the present invention.

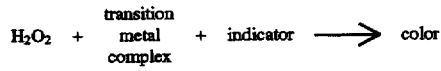

Oxidation-reduction indicators ("redox") indicators are substances which have a different color in the reduced form than in the oxidized form and which can be reversibly reduced and oxidized. Examples of oxidation-reduction indicators which can be used with the transition metal complexes of the present invention are benzidine, o-tolidine, 3,3',5,5'-tetraalkylbenzidines wherein the alkyl group contains from one to six carbon atoms (e.g., 3,3',5,5'-tetramethylbenzidine ("TMB")), o-dianisidine, 2,7-diaminofluorene, bis-(N-ethylquinol-2-one)-azine, (N-methylbenzthiazol-2-one)-(1-ethyl-3-phenyl-5-methyltriazol-2-one)-azine, 2,2'-azinobis(3-ethylbenzothiazoline-6-sulfonic acid), 4-aminoantipyrine, potassium iodine, or combinations thereof.

The pH of the test sample is preferably in the range of from about 3 to about 9, most preferably in the range of from about 4.5 to about 8.2. Hydrogen peroxide may be detected in a test sample in which the concentration of hydrogen peroxide is in the range of from about 0.1 to about 100 mM (millimolar), preferably from about 1 to about 20 mM.

The following examples and data are listed to demonstrate the novelty of the assay as well as its practical use for the detection of hydrogen peroxide. Example 1 is of a dry reagent for the detection of hydrogen peroxide. Example 2 is of a dry reagent for the detection of glucose via the detection of hydrogen peroxide generated from the reaction of glucose with glucose oxidase. Example 3 shows a test of the peroxidase activity various transition metal complexes.

EXAMPLE 1

Reagent for the detection of hydrogen peroxide.

Dry reagent paper was made by sequentially impregnating reagent paper with the components of two dip solutions, drying in between dips. The reagent paper was then dried at 60° C. for approximately 7 minutes. The paper carrier used was Whatman 3 MM. Dip 1 contained iron creatinine and buffer and was prepared by the addition of 100 mL (milliliters) of water to 4.52 g (grams) of creatinine, 2.70 g ferric chloride hexahydrate, and 2.0 g malonic acid, and allowing the mixture to stir overnight; the solution was then adjusted to pH 4.6 using 1N NaOH; final concentrations were 100 mM ferric chloride, 400 mM creatinine, and 250 mM malonic acid. Dip 2 contained the redox indicator, 3,3',5,5'-tetramethylbenzidine ("TMB") at a concentration of 80 mM in acetonitrile.

Reagent strips were made from papers produced from the dips above. The strips were then dipped into urine containing various levels of hydrogen peroxide and the reflectance at 660 nm (nanometers) was measured with an Advanced Research Rapid Scanner instrument at one minute after dipping. The reflectance value was taken to represent reagent reactivity. Reagent reactivity was determined using three urine pools of differing specific gravities, 1.005, 1.015 and 1.023 g/mL.

Reagent color is directly proportional to hydrogen peroxide concentration. The FIGURE shows the linear dose response observed between hydrogen peroxide concentration and the K/S values obtained with the iron-creatinine reagent. The K/S is the conversion from reflectance to units which are proportional to the absorbance by the indicator. It was calculated according to the equation $K/S=(1-R)^2/2R$, wherein R is the reflectance at 660 nm and 1 minute.

Table 2 shows that the reagent reactivity towards 3.0 mg/dL (milligrams per deciliter) hydrogen peroxide (0.88 mM) was fairly consistent in all three urine pools. The reagent remained reactive towards 3.0 mg/dL hydrogen peroxide in the presence of 100 mg/dL ascorbic acid, indicating the oxidation of ascorbate was occurring.

TABLE 2

| | Reflectance at 660 nm and 1 minute Mean (standard deviation) | | |
|---|---|---|---|
| Additive to urine | Urine specific gravity 1.005 g/mL | Urine specific gravity 1.015 g/mL | Urine specific gravity 1.023 g/mL |
| none | 72.4 (0.9) | 70.4 (0.9) | 69.2 (1.1) |
| 3.0 mg/dL $H_2O_2$ | 29.8 (1.2) | 29.9 (2.3) | 36.8 (3.2) |
| 3.0 mg/dL $H_2O_2$ and 100 mg/dL ascorbic acid | 37.9 (2.1)* | 40.8 (1.7)* | 48.0 (1.9)* |

*The reduced reactivity in the presence of ascorbate partly reflects reductive decomposition of hydrogen peroxide by ascorbate in the test solution prior to dipping of reagent.

The data in Table 2 sharply contrasts with a reagent made with horseradish peroxidase instead of iron creatinine (Table 3).

TABLE 3

| | Reflectance at 660 nm and 1 minute Mean (standard deviation) | | |
|---|---|---|---|
| Additive to urine | Urine specific gravity = 1.005 g/mL | Urine specific gravity = 1.015 g/mL | Urine specific gravity = 1.023 g/mL |
| none | 71.3 (0.4) | 72.3 (1.2) | 74.6 (2.1) |
| 3.0 mg/dL $H_2O_2$ | 32.6 (2.3) | 35.3 (4.1) | 39.7 (2.8) |
| 3.0 mg/dL $H_2O_2$ and 100 mg/dL ascorbic acid | 77.2 (0.5) | 76.1 (0.2) | 78.3 (0.3) |

The peroxidase reagent was completely unreactive towards 3.0 mg/dL hydrogen peroxide in the presence of 100 mg/dL ascorbic acid. Reactivity of the iron creatinine reagent increased with decreasing pH and with increasing ratio of creatinine to iron. A ligand ratio of 4 to 1 (creatinine to iron) was selected because of lesser interference from urinary phosphate, thereby providing more consistent results in all urines. A reagent pH of 4.5 was selected because it provided adequate reactivity towards 3.0 mg/dL hydrogen peroxide, which was roughly the amount of hydrogen peroxide expected from the reaction of glucose oxidase on 100 mg/dL glucose. Malonic acid serves as a buffer to control the pH and can be substituted with other buffers such as citrate, tartaric acid, boric acid, succinic acid, glycerol-2-phosphate, salicylic acid, oxalic acid, and malic acid.

EXAMPLE 2

Hydrogen peroxide reactivity was also observed with iron chelates of guanidine. The reactivity was determined by a test done as in Example 1 except that 400 mM guanidine was used in Dip 1 instead of 400 mM creatinine. The specific gravity of the urine was 1.015 g/mL. The results appear in Table 4.

TABLE 4

| | Reflectance at 660 nm and 1 minute Mean (standard deviation) | |
|---|---|---|
| | Additive to urine | |
| Iron Complex | none | 3.0 mg/dL $H_2O_2$ |
| Guanidine 2-ethyl sulfonic acid | 73.4 (3.1) | 43.4 (3.6) |
| Guanidine benzene-3,5- dicarboxylic acid | 71.7 (0.9) | 51.1 (2.7) |
| L-arginine | 72.9 (1.5) | 63.5 (3.0) |

EXAMPLE 3

Reagent for the detection of glucose.

Dry reagent paper was prepared as in Example 1. The first and second dips were prepared as in Example 1 except that 500 units/mL glucose oxidase was also added to the first dip before the pH adjustment.

The reflectance at 660 nm obtained at one minute after dipping the strip in urine containing various levels of glucose was taken to represent reagent reactivity.

Reagent color is directly proportional to glucose concentration. The reagent reactivity towards 100 mg/dL glucose was fairly consistent in all three urine pools (Table 5). The reagent remained reactive towards 100 mg/dL glucose in the presence of 100 mg/dL ascorbic acid, indicating that oxidation of ascorbate was occurring.

TABLE 5

| | Reflectance at 660 nm and 1 minute Mean (standard deviation) | | |
|---|---|---|---|
| Additive to urine | Urine specific gravity = 1.005 g/mL | Urine specific gravity = 1.015 g/mL | Urine specific gravity = 1.023 g/mL |
| none | 68.4 (3.3) | 74.1 (3.1) | 69.7 (2.7) |
| 100 mg/dL glucose | 41.5 (1.2) | 49.1 (2.6) | 47.8 (4.1) |
| 100 mg/dL glucose and 100 mg/dL ascorbic acid | 49.4 (1.6) | 54.5 (3.5) | 57.6 (3.1) |

EXAMPLE 4

Reagent for the detection of hydrogen peroxide using various iron complexes.

Various transition metal complexes were tested for peroxidase activity at pH 5.8 by measuring the oxidation ram of the redox indicator, TMB, for a 3-part water to 2-part acetonitrile solution containing 3.1 mM metal chelate, 44 mM malonic acid, 14 mM diisopropyl dihydroperoxide, and 11.6 mM TMB at pH 5.8. The results shown in Table 6 show iron ($Fe^{2+}$ and $Fe^{3+}$) complexes with poly-L-arginine and creatinine to be the most active. While copper shows some reactivity, it is to a much lower extent (1/10). No other metal (in the list given) showed peroxidase activity under these conditions. Results appear in Table 6.

TABLE 6

| Chelate | Peroxidase Rate (Abs @ 660 nm/min) | | |
|---|---|---|---|
| | $Fe^{2+}$ | $Fe^{3+}$ | $Cu^{2+}$ |
| Fe ammonium | 0.00 | 0.00 | |
| Fe sulfate | 0.00 | 0.00 | |
| Fe EDTA | 0.02 | 0.03 | |
| Fe HEDTA | 0.06 | 0.09 | |
| Fe DTPA | 0.00 | 0.19 | |
| Fe EGTA | 0.00 | 0.00 | |
| Fe CDTA | 0.00 | 0.01 | |
| Fe dipyridine | 0.00 | 0.07 | |
| Fe albumin | 0.03 | 0.00 | |
| Fe poly orithine | 0.03 | 0.05 | |
| Fe poly-D-lysine | 0.03 | 0.04 | |
| Fe poly-L-lysine | 0.04 | 0.06 | |
| Fe poly-L-arginine | 0.12 | 0.19 | |
| Fe poly-L-histidine | 0.08 | 0.12 | |
| Fe poly-L-glycine | 0.01 | 0.02 | |
| Fe L-histidine | 0.03 | 0.05 | |
| Fe creatinine | 0.40 | 0.63 | |
| Cu creatinine | | | 0.05 |

The full chemical names for the abbreviations used in Table 6 are: EDTA: ethylenediaminetriacetic acid; HEDTA: N-(2-hydroxyethyl)ethylenediamine triacetic acid; DTPA: diethylenetriamine pentaacetic acid; EGTA: ethylene bis (oxyethylenenitrilo tetraacetic acid); and CDTA: 1,2-diaminocyclohexane-N,N,N',N'-tetraacetic acid.

What is claimed is:

1. A method for the detection of hydrogen peroxide in a solution which may contain ascorbate, comprising the steps of:

(a) adding to said solution an oxidation-reduction indicator and a transition metal complex having the structure:

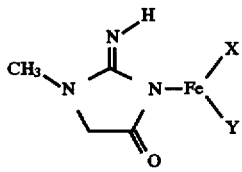

wherein X and Y are independently chosen from the group consisting of creatinine, chloride, fluoride, bromide, iodide, sulfate, phosphate, perchlorate, nitrate, oxalate, sulfide, ammonium, gluconate, cyanide, thiocyanate, catechol, tropolone, phenol, pyridine, acetate, citrate, tartaric acid, malonic acid, boric acid, succinic acid, glycerol-2-phosphate, salicylic acid, oxalic acid, and malic acid; and (b) analyzing the color transition to detect the presence or concentration of hydrogen peroxide.

2. The method of claim 1 wherein X and Y are chloride.

3. The method of claim 1 wherein X and Y are acetate.

4. The method of claim 1 wherein the oxidation-reduction indicator is chosen from the group consisting of benzidine, o-tolidine, 3,3',5,5'-tetraalkylbenzidines having alkyl groups containing from one to six carbon atoms, o-dianisidine, 2,7-diaminofluorene, bis-(N-ethylquinol-2-one)-azine, (N-methylbenzthiazol-2-one)-(1-ethyl-3-phenyl-5-methyltriazol-2-one)-azine, 2,2'-azinobis(3-ethylbenzothiazoline-6-sulfonic acid), 4-aminoantipyrine, potassium iodine, and combinations thereof.

5. The method of claim 4 wherein the oxidation-reduction indicator is 3,3',5,5'-tetramethylbenzidine.

6. The method of claim 1 wherein the solution is a biological fluid or an aqueous solution.

7. The method of claim 1 wherein the solution also contains ascorbate ion.

8. The method of claim 1 wherein the concentration of hydrogen peroxide is in the range of from about 0.1 to about 100 mM.

9. The method of claim 8 wherein the concentration of hydrogen peroxide is in the range of from about 1 to about 50 mM.

10. The method of claim 1 wherein the oxidation-reduction indicator and the transition metal complex are added to the solution by means of a test strip to which they have been applied.

11. A method for the detection of hydrogen peroxide in a solution which may contain ascorbate, comprising the steps of:

(a) adding to said solution an oxidation-reduction indicator and a transition metal complex having the structure:

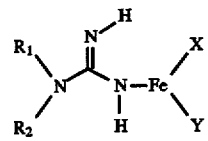

wherein X and Y are independently chosen from the group consisting of creatinine, chloride, fluoride, bromide, iodide, sulfate, phosphate, perchlorate, nitrate, oxalate, sulfide, ammonium, gluconate, cyanide, thiocyanate, catechol, tropolone, phenol, pyridine, acetate, citrate, tartaric acid, malonic acid, boric acid, succinic acid, glycerol-2-phosphate, salicylic acid, oxalic acid, and malic acid, and $R_1$ and $R_2$ are independently chosen from the group consisting of $C_nH_{2n+1}$, $(C_2H_4O)_nH$, $C_5H_4Z$, $C_4H_3Z$, and $C_{11}H_6Z$, wherein n is an integer from 1 to 20, and Z is O, S, N, or CH; and (b) analyzing the color transition to detect the presence or concentration of hydrogen peroxide.

12. The method of claim 11 wherein X and Y are sulfate.

13. The method of claim 11 wherein X and Y are acetate.

14. The method of claim 11 wherein n is an integer from 1 to 12.

15. The method of claim 11 wherein at least one of $R_1$ and $R_2$ is substituted with at least one functional group chosen from the group consisting of alcohol, amine, carbonyl, sulfonic acid, carboxylic acid, fluorine, chlorine, bromine, iodine, phosphonic acid, and phosphate.

16. The method of claim 15 wherein $R_1$ is H and $R_2$ is $CH_2CH_2-SO_3H$.

17. The method of claim 15 wherein $R_1$ is H and $R_2$ is $C_6H_3(CO_2H)_2$.

18. The method of claim 15 wherein $R_1$ is H and $R_2$ is $(CH_2)_3CH(NH_2)CO_2H$.

19. The method of claim 11 wherein the oxidation-reduction indicator is chosen from the group consisting of benzidine, o-tolidine, 3,3',5,5'-tetraalkylbenzidines having alkyl groups containing from one to six carbon atoms, o-dianisidine, 2,7-diaminofluorene, bis-(N-ethylquinol-2-one)-azine, (N-methylbenzthiazol-2-one)-(1-ethyl-3-phenyl-5-methyltriazol-2-one)-azine, 2,2'-azinobis(3-ethylbenzothiazoline-6-sulfonic acid), 4-aminoantipyrine, potassium iodine, and combinations thereof.

20. The method of claim 19 wherein the oxidation-reduction indicator is 3,3',5,5'-tetramethylbenzidine.

21. The method of claim 11 wherein the solution is a biological fluid or an aqueous solution.

22. The method of claim 11 wherein the solution also contains ascorbate ion.

23. The method of claim 11 wherein the concentration of hydrogen peroxide is in the range of from about 0.1 to about 100 mM.

24. The method of claim 23 wherein the concentration of hydrogen peroxide is in the range of from about 1 to about 50 mM.

25. The method of claim 11 wherein the oxidation-reduction indicator and the transition metal complex are added to the solution by means of a test strip to which they have been applied.

* * * * *